(12) United States Patent
Hopps et al.

(10) Patent No.: US 10,448,671 B2
(45) Date of Patent: Oct. 22, 2019

(54) HEATING SYSTEM AND METHOD OF HEATING FOR AN INHALER DEVICE

(71) Applicant: JT International S.A., Geneva (CH)

(72) Inventors: Jason Hopps, Londonderry (GB); Philip Seeney, Cambridge (GB); Colin Turner, Cambridge (GB); Louise Oliver, Welwyn (GB)

(73) Assignee: JT International S.A. (CH)

( * ) Notice: Subject to any disclaimer, the term of this patent is extended or adjusted under 35 U.S.C. 154(b) by 469 days.

(21) Appl. No.: 15/103,769

(22) PCT Filed: Nov. 26, 2014

(86) PCT No.: PCT/EP2014/075593
§ 371 (c)(1),
(2) Date: Jun. 10, 2016

(87) PCT Pub. No.: WO2015/086316
PCT Pub. Date: Jun. 18, 2015

(65) Prior Publication Data
US 2016/0309783 A1 Oct. 27, 2016

(30) Foreign Application Priority Data
Dec. 11, 2013 (EP) .................................... 13196731

(51) Int. Cl.
*A61M 15/06* (2006.01)
*A24F 47/00* (2006.01)

(52) U.S. Cl.
CPC ........... *A24F 47/008* (2013.01); *A61M 15/06* (2013.01)

(58) Field of Classification Search
None
See application file for complete search history.

(56) References Cited

U.S. PATENT DOCUMENTS

| 4,776,515 A | * | 10/1988 | Michalchik | ............... A61L 9/14 239/3 |
| 4,848,374 A | | 7/1989 | Chard et al. | |
| 5,743,251 A | * | 4/1998 | Howell | ................ A61M 11/041 128/200.14 |
| 6,155,268 A | | 12/2000 | Takeuchi | |
| 6,234,167 B1 | * | 5/2001 | Cox | .................. A61M 15/0003 128/200.14 |

(Continued)

FOREIGN PATENT DOCUMENTS

| EP | 2641490 A1 | 9/2013 |
| WO | 2013/027249 A1 | 2/2013 |

OTHER PUBLICATIONS

International Search Report and Written Opinion for Application No. PCT/EP2014/075593, dated Mar. 2, 2015 (9 pages).

*Primary Examiner* — Thor S Campbell
(74) *Attorney, Agent, or Firm* — Lerner, David, Littenberg, Krumholz & Mentlik, LLP

(57) ABSTRACT

A heating system for an inhaler device, such as an e-cigarette or a personal vaporizer, for generating an aerosol and/or a vapor from a substance to be heated includes at least one supply channel for conveying a substance to be heated, especially a liquid solution or a gel, from a supply reservoir by or under capillary action or surface tension forces, and a heater configured to heat the substance as it is conveyed through the at least one channel.

14 Claims, 1 Drawing Sheet

(56) References Cited

U.S. PATENT DOCUMENTS

| | | | |
|---|---|---|---|
| 6,883,516 B2* | 4/2005 | Hindle | A61K 9/007 |
| | | | 128/200.14 |
| 9,271,528 B2* | 3/2016 | Liu | A24F 47/008 |
| 9,289,014 B2* | 3/2016 | Tucker | A24F 47/008 |
| 9,364,027 B2* | 6/2016 | Hon | A24F 47/002 |
| 9,918,496 B2* | 3/2018 | Kane | A24F 47/008 |
| 2013/0199528 A1 | 8/2013 | Goodman et al. | |
| 2013/0213418 A1 | 8/2013 | Tucker et al. | |
| 2014/0000638 A1* | 1/2014 | Sebastian | A24F 47/008 |
| | | | 131/328 |
| 2014/0261488 A1* | 9/2014 | Tucker | A24F 47/008 |
| | | | 131/328 |

* cited by examiner

HEATING SYSTEM AND METHOD OF HEATING FOR AN INHALER DEVICE

Priority is claimed under 35 U.S.C. § 119 to European Application No. 13196731.7 filed on Dec. 11, 2013 and under 35 U.S.C. § 365 to PTC/EP2014/075593 filed on Nov. 26, 2014.

FIELD OF THE INVENTION

The present invention relates to an inhaler device, such as an electronic cigarette (e-cigarette), a personal vaporizer or an electronic vapor delivery system. More particularly, the invention relates to a heating system for such an inhaler device and a method of heating for generating an aerosol and/or a vapor from a substance to be heated in such a device.

BACKGROUND OF THE INVENTION

Inhaler devices of the above types, namely e-cigarettes and personal vaporizers and electronic vapor delivery systems, are proposed as an alternative to traditional smoking articles, such as cigarettes, cigarillos, cigars and the like. Typically, these inhaler devices are designed to heat a liquid solution or a gel to produce or generate an aerosol and/or a vapor to be inhaled by a user. This liquid or gel is usually a solution of propylene glycol (PG) and/or vegetable glycerin (VG), and typically contains a flavorant or one or more concentrated flavors.

Despite the increasing demand for these inhaler devices and the growing market, efforts are still required to develop the performance of these devices, with a view to offering more efficient and improved products. For example, these efforts are directed to an improved aerosol and/or vapor generation, improved aerosol and/or vapor delivery, and more efficient use of energy in aerosol and/or vapor generation to improve the energy consumption, e.g. to enhance the battery life of the device.

SUMMARY OF THE INVENTION

In view of the above, one idea of the present invention is to provide an improved inhaler device, and more particularly an improved heating system and heating method for generating aerosol and/or vapor from a substance in an inhaler device.

According to one aspect, therefore, the invention provides a heating system for an inhaler device, such as an e-cigarette or a personal vaporizer, for generating an aerosol and/or a vapor from a substance to be heated, the system comprising:
at least one supply channel for conveying a substance to be heated, especially a liquid solution or gel, from a supply reservoir by capillary action or by surface tension forces within the at least one channel; and
one or more heater or heating means configured to heat the substance as it passes, or is conveyed, through the at least one channel.

In this way, the invention provides a heating system with which heating of the substance, such as a liquid solution or gel, may be performed or carried out in a distributed manner in the individual supply channels for conveying that liquid or gel substance. Each supply channel thus typically provides a narrow passage or a capillary passage for generating the capillary action or the surface tension forces that convey/s or transport/s the substance along and within each channel. In this regard, each said at least one channel is preferably in the form of a bore or tube providing a capillary passage for flow of the substance to be heated.

Thus, in some embodiments of the invention, the heating system comprises a plurality of supply channels for conveying the substance to be heated under capillary action or surface tension forces, and the heating means is configured to heat the substance as it is conveyed through each supply channel. The at least one supply channel with the one or more heater or heating means may define or form at least a first heating zone for the substance to be heated. The plurality of supply channels and the heating means may therefore together define the first heating zone for the substance to be heated.

In some embodiments of the invention, the heating means comprises at least one first heating element that is provided within the at least one supply channel. In this regard, the first heating element desirably extends along a length of the supply channel. The at least one first heating element may be an electrical heating element for Joule heating or resistance heating. To this end, each first heating element may include one or more of an electrically conductive wire, strip, foil, or conductive coating in the at least one supply channel. For example, such a foil or conductive coating may preferably form a layer or coating on an inner surface of each supply channel. The heating elements preferably comprise a material selected from the group of Nichrome 80/20, Cupronickel (CuNi) alloys, Kanthal (FeCrAl), and molybdenum silicide ($MoSi_2$). Furthermore, the heating elements are desirably powered by an electrical supply, such as a battery, in the inhaler device.

In some embodiments, the heating system of the present invention comprises a housing that accommodates the supply reservoir for the substance to be heated, and a body member that separates the supply reservoir from a vapor chamber and provides fluid communication there-between via the at least one supply channel. With this heating system in an inhaler device, e.g. an e-cigarette or personal vaporizer, a user can then inhale an aerosol and/or vapor formed from by heating of the substance from the vapor chamber. Preferably, the at least one supply channel is formed in a periphery of and/or through the body member. Accordingly, each of the first heating elements is also preferably provided in or on the body member. The first heating elements may also be interconnected by electrically conductive bridges in or on said body member.

In this way, the supply channels in or on the body member having the one or more heater or heating means for heating the substance as it passes or is conveyed through those supply channels may together form a (first) heating zone for the substance to be heated. Furthermore, as the body member preferably separates the supply reservoir from a main (second) heating zone for vaporization of the substance (i.e. liquid solution or gel), each supply channel is thus typically configured to convey or transport the substance from the supply reservoir to the main (second) heating zone. In this way, the (first) heating zone of the supply channels may serve to preheat and expand the substance only. The preheated substance is therefore able to migrate to the second heating zone after preheating. That is, the preheated substance may begin to boil or vaporize in the first heating zone and expands (e.g. as vapor, thermally expanding liquid, or discrete liquid droplets) along the one or more channels into the second heating zone.

In some embodiments, the body member is comprised of an electrically insulating material. The supply channels are advantageously formed as fine or narrow bores or capillary passages having a diameter in the range of 0.1 to 2.0 mm, and preferably in the range of 0.1 to 1.0 mm, i.e. small and precisely dimensioned. The body member nay also be formed of a material that may be machined or manufactured with precision. A ceramic material may be chosen for the body member, as it may satisfy both of the requirements, as well as being very temperature resistant. Other materials, such as polymer plastics, silicates, or similar materials may also be contemplated, however.

In some embodiments, therefore, a main (i.e. second) heating zone may be provided as a single chamber or cavity within the housing of the system, and each supply channel is provided in fluid communication therewith. In an alternative embodiment, however, the second heating zone may include a number of second heating cavities, with at least one supply channel in fluid communication with a respective one of the second heating cavities. The main or second heating zone preferably includes at least one second heating element, which may again be an electrical element, such as a wire, ribbon, strip, foil, or conductive coating for Joule heating or resistance heating. Such a wire or coil may extend through each second heating cavity. In the case of a foil or coating, however, this may be provided as a film deposit or lining on a surface of each second heating cavity.

In this way, the heating system of the invention may provide two-stage heating for the inhaler device. An initial heating or "preheating" of the substance (e.g. liquid or gel) occurs in the first heating zone, i.e. in the supply channels of the body member separating the supply reservoir from the main or second heating zone. Here the substance may be subject to pressurization, possibly even boil and partially vaporize, and will typically undergo a thermal expansion. The thermal expansion may generate a localized pressure increase in the first heating zone, which then forces or drives the substance under pressure towards the second heating zone. In such a case, the substance may be comprised of an aerosol, droplets, and/or suspension of the liquid solution or gel to be heated and/or a vapor thereof. The substance is further vaporized in the second heating zone and undergoes a volumetric expansion during the phase change to gas. Each second heating cavity may communicate with at least one nozzle for delivery of the vapor and/or aerosol produced to a mouthpiece of the inhaler device. Thus, due to the preheating, the heating required to carry out full vaporization of the substance in the second heating zone can be achieved both quickly and efficiently.

In some embodiments, the first heating zone or supply channels may receive the substance to be heated (e.g. liquid or gel) from the supply reservoir via a feed mechanism. The feed mechanism may include one or more of capillary action and pressure bias. A pressure bias may be created by applying pressure to the liquid or gel substance stored in the supply reservoir, such that it is biased from the reservoir towards the first heating zone or supply channels. Alternatively, or in addition, the supply reservoir may be flexible or collapsible for applying a pressure bias, and/or may include a vent such that suction and capillary action create a pressure bias between the reservoir and the supply channels promoting migration of the substance. Furthermore, the feed mechanism may be configured to vary a feed rate of the substance from the supply reservoir. To this end, the feed mechanism of the heating system may include a valve mechanism to regulate the feed rate of the substance. The feed rate may be set or adjusted by a user to match or suit an inhalation profile of the user. A valve mechanism could then be used to shut-off transfer or conveyance of the liquid or gel from the supply reservoir when the inhaler device is not in use, e.g. when it is switched off.

In some embodiments, the housing that accommodates the support body includes one or more air inlets, such that air may be drawn in and mixed with the vaporized substance as it is transformed to a vapour. The one or more air inlets may direct air into the second heating zone, or may alternatively be provided either upstream and/or downstream of the second heating zone. Thus, in a particular embodiment, the housing may include a plurality of holes extending (e.g. radially) through a side wall of the housing into each second heating cavity. The one or more air inlets or the inlet holes may serve to provide a balancing air-flow; i.e. to create a desired air-flow resistance for a user when the system is incorporated in an inhaler device. Preferably, the one or more air inlets can be selectively changed or adjusted by a user, e.g. by modifying an air inlet size, to regulate a mix of inlet air and the aerosol and/or vapour to be inhaled and to modify the flow resistance of the device.

According to a further aspect, the present invention provides an inhaler device, especially an electronic cigarette or a personal vaporizer, for generating an aerosol and/or vapor from a substance to be heated, such as a liquid solution or a gel, wherein the inhaler device includes a heating system according to any one of the embodiments described above.

According to yet another aspect, the invention provides a method of heating a substance, especially a liquid solution or a gel, in an inhaler device, such as an e-cigarette or a personal vaporizer, the method comprising:
conveying the substance to be heated from a supply reservoir through at least one supply channel by capillary action or surface tension forces;
heating the substance in the at least one supply channel as the substance is conveyed there-through.

In some embodiments of the invention, the step of heating the substance in the at least one supply channel is performed by one or more electrical heating element provided in each supply channel. As noted above, each heating element may respectively comprise an electrical resistance element, such as a wire, ribbon, strip, foil, or a conductive coating, for Joule heating or resistance heating. Each heating element is therefore desirably powered by an electrical supply, such as a battery, in the inhaler device.

In some embodiments, the step of heating the substance in the at least one supply channel is performed or carried out on a periodical or intermittent basis; for example, in a pulsed or in an alternating manner.

In some embodiments, the step of conveying the substance to be heated from a supply reservoir through at least one supply channel involves conveying the substance to a main heating zone for vaporization of the substance. In this way, the step of heating the substance in the at least one supply channel as it is conveyed comprises a preheating of the substance in a first heating zone. The method of this embodiment therefore includes the further step of heating the substance in the main (second) heating zone to form a vapor, which then typically condenses to form an aerosol. The step of heating the substance in the second heating zone may also be performed by one or more electrical heating elements.

In some embodiments, each of the preheating and heating steps may be carried out periodically or sequentially. That is, each of the heating zones may be activated or powered in an alternating or pulsed manner in specific or predetermined activation intervals or periods. For example, an activation period of 50 msec could be applied to power or activate each of the first heating elements for this period, followed by an activation period of 50 msec for each second heating element. Such a pulsed activation of the heating elements can provide improved energy consumption.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which.

DETAILED DESCRIPTION OF EMBODIMENTS OF THE INVENTION

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will further be appreciated that certain actions and/or steps in an embodiment of a method may be described or depicted in a particular order of occurrences while those skilled in the art will understand that such specificity with respect to sequence is not actually required. It will also be understood that the terms and expressions used in the present specification have the ordinary meaning as is accorded to such terms and expressions with respect to their corresponding respective areas of inquiry and study, except where specific meanings have otherwise been set forth herein.

With reference to FIGS. 1 to 5 of the drawings, a part of an inhaler device 1 embodied as an electronic cigarette (also known as an "e-cigarette") is represented schematically. This inhaler device 1 includes a casing 2 provided in the form of a generally cylindrical sleeve, which accommodates a heating system 3 according to the invention. The heating system 3 is designed for heating a liquid solution or gel L supplied from a reservoir 4 in the inhaler device 1 to generate an aerosol and/or vapor V for inhalation by a user as a substitute for smoking traditional cigarettes. To this end, the liquid L may include a solution of propylene glycol, vegetable glycerin, a flavorant, and/or one or more flavours.

Figure 1:
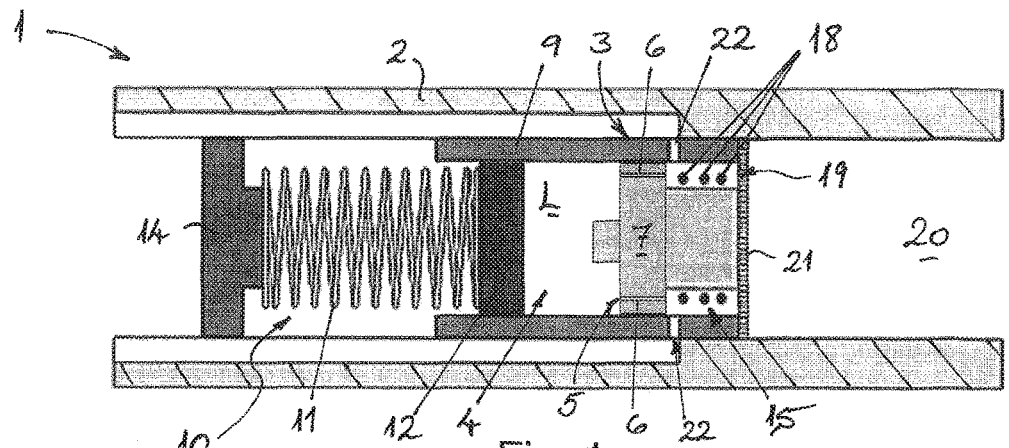
FIG. 1 is a schematic cross-sectioned side view of a heating system in an inhaler device according to an embodiment of the invention.

The heating system 3 of this embodiment provides two-step or two-stage heating of the liquid L to generate or produce the aerosol and/or vapor V for inhalation. In particular, with reference also to FIGS. 2 and 3 of the drawings, the heating system 3 includes a first heating zone 5 which comprises a plurality of supply channels 6 formed in and through a body member or plug member 7 having a generally cylindrical shape, and a number of first heating elements 8 in the form of metal wires which extend through each of the supply channels 6. As seen in FIG. 1, this body member 7 is optionally accommodated within a generally cylindrical housing 9.

Figures 2, 3, 4:
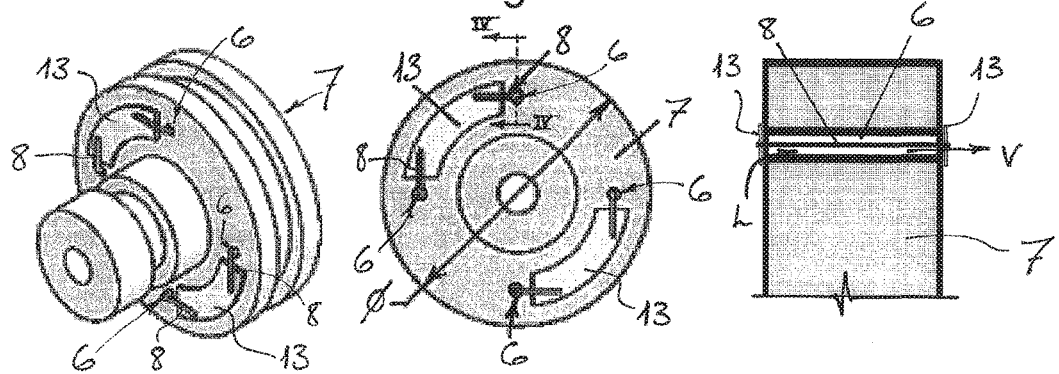
FIG. 2 is a schematic perspective view of part of a heating system according to an embodiment of the invention.
FIG. 3 is a schematic end view of that part of the heating system in FIG. 2.
FIG. 4 is a schematic partial cross-section view in the direction of arrows IV-IV in FIG. 3.

As seen in drawing FIGS. 2 and 3, the supply channels 6 are provided as fine bores or passages having a diameter in the range of about 0.1 mm to 2.0 mm, preferably in the range of 0.1 mm to 1.0 mm (e.g. a diameter of about 0.5 mm), which are drilled to extend generally axially through the body member 7 for conveying the liquid solution L from a supply reservoir 4 by capillary action, i.e. by surface tension forces. The body member 7 itself in this case has a diameter $\varphi$ of about 12 mm. The capillary channels 6 of the first heating zone 5 are configured to receive the liquid L from the adjacent supply reservoir 4 via direct contact ensured by a feed mechanism 10 for delivering the liquid L in the supply reservoir 4 to the first heating zone 5. In the present case, the feed mechanism applies pressure to the liquid L in the reservoir 4 via a spring 11 which acts on a movable piston 12.

The heating elements 8 provided in this case are comprised of Nichrome 80/20 wires which are joined or interconnected on a face of the body member 7 by conductive bridges 13. The wire heating elements 8 are preferably arranged such that they are not in contact with the internal surface of the channels 6, but rather extend freely (i.e. spaced from the internal surface) substantially centrally or along a longitudinal axis of the channels 6, as seen in FIG. 4. This can advantageously limit or minimise the formation of deposits and residues in a channel 6 from the liquid L being heated. As an alternative, however, the first heating elements 8 could also comprise conductive foil, e.g. molybdenum silicide ($MoSi_2$), deposited as a film over a surface of each channel 6.

Thus, the bridges 13 interconnecting the heating elements 8 conduct electric current to each of the wires 8 that extend through the capillary bores 6, but do not themselves perform any heating. The heating wires 8 are in intimate contact with the liquid L as it is passes from the supply reservoir 4 through and along the supply channels 6 by or under capillary action. These first heating elements or wires 8 are provided with electrical energy from a battery 14 and are thereby heated when the inhaler device 1 is switched on or activated to effect a preheating of the liquid L in the first heating zone 5. As the liquid L in the first heating zone 5 undergoes initial heating, it may begin to boil or at least expand and become pressurized, such that it is transferred or conveyed by both capillary action and by thermal expansion to a second heating zone 15, as well as by the influence of an influx of new liquid L into the first heating zone 5 or channels 6 from the reservoir 4. Thus, the liquid L is already preheated as it emerges from the channels 6 into a main heating chamber 16, which forms a main or second heating zone 15 of the heating system 3 of the invention.

Thus, in this embodiment, the second heating zone 15 includes a heating cavity 16 and at least one second heating element 18 for electrically heating the liquid L when it enters the second heating zone. The second heating element 18 in this example comprises a wire coil and, as with the first heating elements 8, may again be formed from Nichrome 80/20 wire. In any case, the second heating element 18 further heats the preheated liquid L to effect its full vaporization in the chamber or cavity 16, in which gas formed by the vaporization of the liquid L may expand. For this reason , the second heating cavity 16 may terminate in or communicates with a nozzle 19 at an end face of body member 7, through which the vapor V is emitted into a vapor chamber 20 from which the user may inhale that aerosol and/or vapour V via a mouthpiece (not shown) of the inhaler device 1. Optionally, a foil 21 with multiple micro-openings or holes may be provided over an end region of the body member 7 and housing 9 facing vapor chamber 20. This foil 21 may, for example, form a filter membrane for the aerosol and vapor V emitted from the heating system 3. At the same time, the foil 21 may provide air-flow resistance, whereby a pressure difference develops across the array and the gas emitted undergoes an expansion and vapour-phase cooling to form inhalable aerosol droplets.

Figure 5:
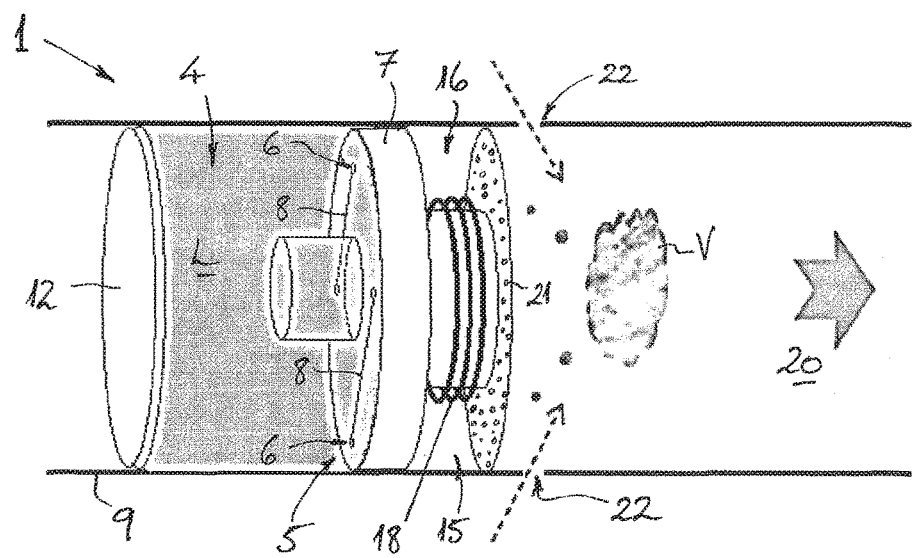
FIG. 5 is a schematic perspective view of the heating system in the inhaler device of FIG. 1.

As is also apparent from FIG. 1 of the drawings, radial air inlets 22 may be provided through the side wall 8 of the housing 9 into the second heating cavity 16 to enable the influx and mixture of air with the vapour V in the second heating zone 15. This may assist with ensuring that a proper flavour or concentration balance is provided in the aerosol and/or vapor V produced. Furthermore, the radial inlets 22 may be used to balance the airflow through the device to provide a desired airflow resistance or "inhalation feel" for the user. Also, this may assist to cool the aerosol or vapour V before it reaches the user via a mouthpiece of the inhaler device 1. It will be noted that air inlets may also be provided downstream of the nozzles 19, e.g. in the vapor chamber 20, to balance or control the flow. With reference to FIG. 5, for example, it will be seen that air inlets 22 may be provided opening radially into the vapor chamber 20 downstream of the second heating zone 15, instead of (or in addition to) into the second heating cavity 17 directly.

It will be noted that cylindrical body member 7 is desirably comprised of a ceramic material that is pre-machined or fabricated to form the supply channels 6 providing the fluid communication between the supply reservoir 4 and the second heating zone 15. As the ceramic body member 7 also supports the first and second electrical heating elements 8, 18, the electrical insulating properties of the ceramic material are relevant to a desired and proper functioning of this heating system 3.

It will also be noted that the heating system 3 shown in this embodiment may optionally be provided in a cartridge designed to be inserted into the casing 2 of the inhaler device 1. That is, the housing 9 incorporating the supply reservoir 4 of the liquid L and the heating system 3 described above may be provided as a replaceable (e.g. disposable) cartridge, so that once the supply reservoir 4 of the liquid L to be heated is depleted or exhausted, that cartridge may be removed and a replacement cartridge may then be inserted into the casing 2 of the inhaler device 1 in its place. The depleted cartridge could then either be re-filled with liquid L to be used again or simply disposed of.

Although specific embodiments of the invention have been illustrated and described herein, it will be appreciated by those of ordinary skill in the art that a variety of alternate and/or equivalent implementations exist. It should be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

Also, it will be appreciated that in this document, the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and an used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

What is claimed is:

1. A heating system for an inhaler device for generating an aerosol and/or a vapor from a substance to be heated, the system comprising:
    a supply reservoir bounded by inner surfaces;
    a body member having a first surface facing in an axial direction and a second surface facing away from the first surface, the first surface of the body member being one of the inner surfaces of the supply reservoir;
    at least one supply channel being a first heating zone extending from the first surface of the body member to the second surface of the body member, the at least one supply channel configured to convey a substance to be heated out of the supply reservoir under capillary action or surface tension forces within the at least one supply channel;
    at least one first heating element configured to heat the substance as it is conveyed through the at least one supply channel, the at least one first heating element extending into an interior volume of the at least one supply channel; and
    a second heating zone configured to vaporize the substance, the second heating zone separated from the supply reservoir by the body member and partially bounded by the second surface of the body member.

2. The heating system of claim 1, wherein the at least one first heating element extends along a length of the at least one supply channel.

3. The heating system of claim 2, wherein the at least one first heating element includes one or more of an electrically conductive wire, strip, foil, or conductive coating in the at least one supply channel; the foil or conductive coating forming a layer or coating on an inner surface of the at least one supply channel.

4. The heating system of claim 1, wherein the at least one supply channel comprises a plurality of supply channels for conveying the substance to be heated under capillary action or surface tension forces; wherein the at least one first heating element is configured to heat the substance as it is conveyed through each supply channel; and wherein the plurality of supply channels and the at least one first heating element together define the first heating zone for the substance to be heated.

5. The heating system of claim 1, wherein the body member separates the supply reservoir from a vapor chamber from which the aerosol and/or vapor is inhaled.

6. The heating system of claim 5, wherein the heating elements are interconnected by electrically conductive bridge elements provided in or on the body member.

7. The heating system of claim 1, wherein the second heating zone includes one or more second heating cavities, and wherein at least one of the supply channels is in fluid communication with a respective one of the second heating cavities.

8. The heating system of claim 1, wherein the at least one supply channel has a diameter in the range of 0.1 to 2.0 mm.

9. The heating system of claim 1, further comprising a housing that accommodates the supply reservoir therein for the substance to be heated.

10. The heating system of claim 1, further comprising a feed mechanism configured to deliver the substance to be heated from the supply reservoir; wherein the feed mechanism generates fluid pressure in the supply reservoir.

11. An inhaler device for producing aerosol and/or vapor form a substance to be heated, wherein the inhaler device includes a heating system, the heating system comprising:
- a supply reservoir bounded by inner surfaces;
- a body member having a first surface facing in an axial direction and a second surface facing away from the first surface, the first surface of the body member being one of the inner surfaces of the supply reservoir;
- at least one supply channel being a first heating zone extending from the first surface of the body member to the second surface of the body member, the at least one supply channel configured to convey a substance to be heated out of the supply reservoir under capillary action or surface tension forces within the at least one supply channel;
- at least one first heating element configured to heat the substance as it is conveyed through the at least one supply channel, the at least one first heating element extending into an interior volume of the at least one supply channel; and
- a second heating zone configured to vaporize the substance, the second heating zone separated from the supply reservoir by the body member and partially bounded by the second surface of the body member.

12. A method of heating a substance in an inhaler device having a body member and a supply reservoir, the method comprising:
- conveying the substance to be heated from a supply reservoir through at least one supply channel by capillary action or surface tension forces, wherein the body member has a first surface facing in an axial direction and a second surface facing away from the first surface, the first surface of the body member being an inner surface of the supply reservoir;
- heating the substance in the at least one supply channel as the substance is conveyed there-through, the at least one supply channel being a first heating zone extending from the first surface of the body member to the second surface of the body, the heating performed by at least one first heating element that is extending into an interior volume of the at least one supply channel; and
- heating the substance in a second heating zone configured to vaporize the substance, the second heating zone separated from the supply reservoir by the body member and partially bounded by the second surface of the body member.

13. The method of claim 12, wherein the at least one first heating element comprises one or more electrical heating elements provided in each supply channel.

14. The method of claim 12, wherein the step of heating the substance in the at least one supply channel is carried out on a periodical or intermittent basis.

* * * * *